United States Patent
Kang et al.

(10) Patent No.: US 11,667,297 B2
(45) Date of Patent: Jun. 6, 2023

(54) VEHICLE CONTROLLING METHOD AND APPARATUS USING ERROR MONITORING

(71) Applicants: HYUNDAI MOTOR COMPANY, Seoul (KR); KIA MOTORS CORPORATION, Seoul (KR); SOOKMYUNG WOMEN'S UNIVERSITY INDUSTRY—ACADEMIC COOPERATION FOUNDATION, Seoul (KR)

(72) Inventors: Jeong Su Kang, Seongnam-si (KR); Suh Yeon Dong, Seoul (KR)

(73) Assignees: HYUNDAI MOTOR COMPANY, Seoul (KR); KIA MOTORS CORPORATION, Seoul (KR); SOOKMYUNG WOMEN'S UNIVERSITY INDUSTRY—ACADEMIC COOPERATION FOUNDATION, Seoul (KR)

( * ) Notice: Subject to any disclaimer, the term of this patent is extended or adjusted under 35 U.S.C. 154(b) by 358 days.

(21) Appl. No.: 16/906,191

(22) Filed: Jun. 19, 2020

(65) Prior Publication Data
US 2020/0406901 A1 Dec. 31, 2020

(30) Foreign Application Priority Data
Jun. 26, 2019 (KR) .................. 10-2019-0076122

(51) Int. Cl.
| | | |
|---|---|---|
| B60W 40/08 | (2012.01) | |
| B60W 50/00 | (2006.01) | |
| A61B 5/18 | (2006.01) | |
| A61B 5/316 | (2021.01) | |

(52) U.S. Cl.
CPC .............. *B60W 40/08* (2013.01); *A61B 5/18* (2013.01); *A61B 5/316* (2021.01); *B60W 50/0098* (2013.01)

(58) Field of Classification Search
None
See application file for complete search history.

(56) References Cited

U.S. PATENT DOCUMENTS

2011/0279676 A1* 11/2011 Terada .................. G08B 21/02
 348/148
2015/0310750 A1* 10/2015 Glaunsinger .......... A61B 5/164
 434/258

* cited by examiner

*Primary Examiner* — Thomas S McCormack
(74) *Attorney, Agent, or Firm* — Lempia Summerfield Katz LLC

(57) ABSTRACT

A mobility controlling method and apparatus based on error monitoring are provided. The mobility controlling method includes: collecting an Event-Related Potential (ERP) for at least one passenger in a mobility for a predetermined time, determining an error factor by analyzing the ERP that is collected for the predetermined time, and performing mobility feedback based on the error factor.

20 Claims, 9 Drawing Sheets

−9.3µN     −0.6µN

−1.8µN     13.0µN

VEHICLE CONTROLLING METHOD AND APPARATUS USING ERROR MONITORING

CROSS REFERENCE TO RELATED APPLICATION

This application claims priority to and the benefit of Korean Patent Application No. 10-2019-0076122, filed Jun. 26, 2019, the entire contents of which are incorporated herein f by reference.

FIELD

The present disclosure relates to a mobility controlling method and apparatus. More particularly, the present disclosure relates to a mobility controlling method and apparatus based on error monitoring.

BACKGROUND

The statements in this section merely provide background information related to the present disclosure and may not constitute prior art.

As one of the transport means, a vehicle (or mobility) is a very important means and tool for living a life in the modern world. Furthermore, a vehicle itself may be regarded as something special that gives meaning to someone.

As technology is advanced, functions provided by a vehicle also gradually evolve. For example, in recent years, vehicles not only transport a passenger to a destination, but also meet a passenger's needs for faster and safer travel to a destination. In addition, new devices are being added to a vehicle system in order to satisfy a passenger's aesthetic taste and comfort. In addition, the existing devices like steering wheels, transmissions and acceleration/deceleration devices are also being developed so that more functions can be provided to users.

Meanwhile, a brain-computer interface or a brain-machine interface is a field of controlling a computer or a machine according to a person's intention by using brain wave signals. ERP (Event-Related Potential) is closely related to cognitive functions.

SUMMARY

The present disclosure provides a mobility controlling method and apparatus using error monitoring.

In another form, the present disclosure provides a mobility controlling method and apparatus that perform error monitoring using a response-locked ERP (Event-Related Potential) and thus reflect a passenger's needs.

The technical objects of the present disclosure are not limited to the above-mentioned technical objects, and other technical objects that are not mentioned will be clearly understood by those skilled in the art through the following descriptions.

According to one form of the present disclosure, a mobility controlling apparatus may include: a sensing unit that collects an ERP from at least one passenger in a mobility for a predetermined time, an error monitoring unit that analyzes the collected ERP and determines an error factor based on the analyzed ERP of the passenger, and a controlling unit that performs a mobility feedback based on the error factor.

In some forms of the present disclosure, the event-related potential (ERP) may include at least one of ERN (Error-Related Negativity) or Pe (Error Positivity).

In some forms of the present disclosure, the event-related potential (ERP) may further include at least one of CRN (Correct-Related Negativity) and Pc (Correct Positivity).

In some forms of the present disclosure, the error monitoring unit may determine the error factor based on ERPs collected from at least one of the passenger causing the ERP, another person other than the passenger, and an operation of a mobility that is different from the mobility.

In some forms of the present disclosure, the mobility feedback may be controlling a predetermined apparatus included in the mobility.

In some forms of the present disclosure, the error monitoring unit may compare the amplitude of the ERP, which is collected for the predetermined time, with a predetermined threshold.

In some forms of the present disclosure, the predetermined threshold may be differently determined according to at least one of the type of the ERP and the passenger from whom the ERP is obtained.

In some forms of the present disclosure, when the amplitude of the ERP collected for the predetermined time goes beyond the predetermined threshold range, the error monitoring unit may determine a predetermined event as an error factor regarding the passenger.

In some forms of the present disclosure, the predetermined event is derived from a mapping relationship between a plural of events and a comparison result between the amplitude of the ERP and the predetermined threshold.

In some forms of the present disclosure, the predetermined threshold may include a first threshold and a second threshold, the predetermined event may include a first event, a second event and a third event. When the amplitude of the collected ERP exceeds the first threshold, the predetermined event may be mapped with the first event. When the amplitude of the collected ERP is smaller than the second threshold, the predetermined event may be mapped with the third event. When the predetermined event is neither the first event nor the third event, it may be mapped with the second event.

In some forms of the present disclosure, the sensing unit may measure a brain wave signal of at least one passenger in the mobility and detect the ERP from the measured brain wave signal. The ERP may include a response-locked ERP.

In some forms of the present disclosure, the analysis may be judging whether or not the amplitude of the collected ERP is within a predetermined threshold range during a predetermined time interval.

In some forms of the present disclosure, the analysis is performed by using a brain wave signal template for the at least one passenger. The brain wave signal template may be a brain wave signal in a time domain, which is previously obtained within a predetermined time range after the error factor occurs.

In addition, according to one form of the present disclosure, a mobility controlling method may include: collecting, by a sensing unit, an ERP from at least one passenger in a mobility for a predetermined time; determining, by an error monitoring unit, an error factor by analyzing the collected ERP for the predetermined time; and performing, by a control unit, a mobility feedback based on the error factor.

In some forms of the present disclosure, the event-related potential (ERP) may include at least one of ERN (Error-Related Negativity) and Pe (Error Positivity).

In some forms of the present disclosure, the event-related potential (ERP) may further include at least one of CRN (Correct-Related Negativity) and Pc (Correct Positivity).

In some forms of the present disclosure, the error factor may include at least one among the passenger causing the ERP, another person other than the passenger, and an operation of a mobility that is different from the mobility.

In some forms of the present disclosure, the mobility feedback may be controlling a predetermined apparatus included in the mobility.

In some forms of the present disclosure, the analysis may be comparing the amplitude of the ERP, which is collected for the predetermined time, and a predetermined threshold.

In some forms of the present disclosure, the predetermined threshold may be differently determined according to at least one of the type of the ERP and the passenger from whom the ERP is obtained.

In some forms of the present disclosure, the determining of an error factor by analyzing an ERP collected for the predetermined time may include determining a predetermined event as an error factor regarding the passenger, when the amplitude of the collected ERP collected for the predetermined time is greater than the predetermined threshold.

In some forms of the present disclosure, the predetermined event is derived from a mapping relationship between a plural of events and a comparison result between the amplitude of the ERP and the predetermined threshold.

In some forms of the present disclosure, the predetermined threshold may include a first threshold and a second threshold, the predetermined event may include a first event, a second event and a third event. When the amplitude of the collected ERP exceeds the first threshold, the predetermined event may be mapped with the first event. When the amplitude of the collected ERP is smaller than the second threshold, the predetermined event may be mapped with the third event. When the predetermined event is neither the first event nor the third event, it may be mapped with the second event.

According to one form of the present disclosure, the collecting of an ERP for at least one passenger in the mobility for a predetermined time may include measuring a brain wave signal of the at least one passenger in the mobility and detecting the ERP from the measured brain wave signal. The ERP may include a response-locked ERP.

According to one form of the present disclosure, the analysis may be judging whether or not the amplitude of the ERP is within a predetermined threshold range during a predetermined time interval.

According to another form of the present disclosure, the analysis is performed by using a brain wave signal template for the at least one passenger. The brain wave signal template may be a brain wave signal in a time domain, which is previously obtained within a predetermined time range after the error factor occurs.

The features briefly summarized above with respect to the present disclosure are merely exemplary aspects of the detailed description below of the present disclosure, and do not limit the scope of the present disclosure.

According to one form of the present disclosure, a mobility controlling method and apparatus using error monitoring may be provided.

In addition, a mobility controlling method and apparatus may be provided which perform error monitoring using a response-locked ERP and thus reflect a passenger's needs Effects obtained in the present disclosure are not limited to the above-mentioned effects, and other effects not mentioned above may be clearly understood by those skilled in the art from the following description.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
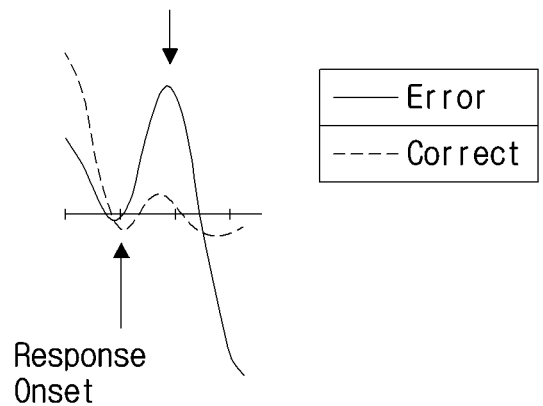
FIG. 1 is a view illustrating a general waveform of ERN in one form of the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Exemplary forms of the present disclosure will be described in detail such that the ordinarily skilled in the art would easily understand and implement an apparatus and a method provided by the present disclosure in conjunction with the accompanying drawings. However, the present disclosure may be embodied in various forms and the scope of the present disclosure should not be construed as being limited to the exemplary forms.

In describing forms of the present disclosure, well-known functions or constructions will not be described in detail when they may obscure the spirit of the present disclosure.

In the present disclosure, it will be understood that when an element is referred to as being "connected to", "coupled to", or "combined with" another element, it can be directly connected or coupled to or combined with the another element or intervening elements may be present therebetween. It will be further understood that the terms "comprises", "includes", "have", etc. when used in the present disclosure specify the presence of stated features, integers, steps, operations, elements, components, and/or combinations thereof but do not preclude the presence or addition of one or more other features, integers, steps, operations, elements, components, and/or combinations thereof.

It will be understood that, although the terms "first", "second", etc. may be used herein to describe various elements, these elements should not be limited by these terms. These terms are only used to distinguish one element from another element and not used to show order or priority among elements. For instance, a first element discussed below could be termed a second element without departing from the teachings of the present disclosure. Similarly, the second element could also be termed as the first element.

In the present disclosure, distinguished elements are termed to clearly describe features of various elements and do not mean that the elements are physically separated from each other. That is, a plurality of distinguished elements may be combined into a single hardware unit or a single software unit, and conversely one element may be implemented by a plurality of hardware units or software units. Accordingly, although not specifically stated, an integrated form of various elements or separated forms of one element may fall within the scope of the present disclosure. Also, the terms, such as 'unit' or 'module', etc., should be understood as a unit that processes at least one function or operation and that may be embodied in a hardware manner (e.g., a processor), a software manner, or a combination of the hardware manner and the software manner.

In the present disclosure, all of the constituent elements described in various forms should not be construed as being essential elements but some of the constituent elements may be optional elements. Accordingly, forms configured by respective subsets of constituent elements in a certain form also may fall within the scope of the present disclosure. In addition, forms configured by adding one or more elements to various elements also may fall within the scope of the present disclosure.

As an electrical activity of neurons constituting a brain, a brain wave signal (or brain signal, brain wave) means a bio signal that directly and indirectly reflects a conscious or nonconscious state of a person. A brain wave signal can be measured in every area of human scalp, and its wavelength has a frequency of mainly 30 Hz or below and a potential difference of scores of microvolts. Depending on brain activity and state, various waveforms may appear. A research on interface control using a brain wave signal according to a person's intention is under way. A brain wave signal may be obtained by using EEG (Electro Encephalo Graphy) using electrical signals caused by brain activities, MEG (Magneto Encephalo Graphy) using magnetic signals occurring with electrical signals, and fMRI (functional Magnetic Resonance Imaging) or fNIRS (Near-Infrared Spectroscopy) using a change of oxygen saturation in the blood. Although fMRI and fNIRS are useful techniques for measuring brain activities, fMRI has a low time-resolution and fNIRS has a low spatial-resolution in general. Due to these limitations, EEG signals are mostly used by virtue of excellent portability and time-resolution.

A brain wave signal changes spatially and over time according to brain activity. As a brain wave signal is usually difficult to analyze and its waveform is not easy to visually analyze, various processing methods are proposed.

For example, according to the number of oscillations (frequency), brain wave signals may be classified based on frequency bands (Power spectrum classification). The classification considers a measured brain wave signal as a linear sum of simple signals at each specific frequency, decomposes the signal into each frequency component and indicates a corresponding amplitude. A brain wave signal at each frequency may be obtained by using pre-processing normally for noise elimination, the Fourier transform into frequency domain, and a band-pass filter (BPF).

More particularly, according to frequency band, brain waves may be classified into delta, theta, alpha, beta and gamma waves. Delta waves are brain waves with a frequency of 3.5 Hz or below and an amplitude of 20~200 pV, mainly appearing in normal deep sleep or newborns. In addition, delta waves may increase as our awareness of the physical world decreases. Generally, theta waves are brain waves with a frequency of 3.5~7 Hz, mainly appearing in emotionally stable states or in sleep.

In addition, theta waves are generated mainly in the parietal cortex and in the occipital cortex and may appear during calm concentration for recollecting a memory or meditating. Generally, alpha waves are brain waves with a frequency of 8~12 Hz, mainly appearing in relaxed and comfortable states. In addition, alpha waves are normally generated in the occipital cortex during rest and may diminish in sleep. Generally, beta waves are brain waves with a frequency of 13~30 Hz, mainly appearing in a state of tension, which is bearable enough, or while a certain level of attention is paid. In addition, beta waves are mainly generated in the frontal cortex and are related to an awakened state or concentrated brain activities, pathological phenomena and medicinal effects. Beta waves may appear in a wide area throughout the brain. In addition, specifically, the beta waves may be divided into SMR waves with a frequency of 13~15 Hz, mid-beta waves with a frequency of 15~18 Hz and high beta waves with a frequency of 20 Hz and above. As beta waves appear to be stronger under stress like anxiety and tension, they are called stress waves. Gamma waves are brain waves that generally have a frequency of 30~50 Hz, mainly appearing in a strongly excited state or during high-level cognitive information processing. In addition, gamma waves may appear in an awaking state of consciousness and during REM sleep and may also be overlapped with beta waves.

Each of the brain wave signals according to frequency band is associated with a specific cognitive function. For example, delta waves are associated with sleep, theta waves are associated with working memory, and alpha waves are associated with attention or inhibition. Thus, the property of a brain wave signal at each frequency band selectively displays a specific cognitive function. In addition, the brain wave signal at each frequency band may show a little different aspect in each measuring part on the surface of head. The cerebral cortex may be divided into frontal cortex, parietal cortex, temporal cortex and occipital cortex. These parts may have a few different roles. For example, the occipital cortex corresponding to the back of head has the primary visual cortex and thus can primarily process visual information. The parietal cortex located near the top of head has the somatosensory cortex and thus can process motor/sensory information. In addition, the frontal cortex can process information related to memory and thinking, and the temporal cortex can process information related to auditory sense and olfactory sense.

Meanwhile, for another example, a brain wave signal may be analyzed by using ERP (Event-Related Potential). ERP is an electrical change in a brain in association with a stimulus from outside or a psychological process inside. ERP means a signal including an electrical activity of the brain, which is caused by a stimulus including specific information (for example, image, voice, sound, command of execution, etc.) after a certain time since the stimulus is presented.

To analyze an ERP, a process of separating a signal from a noise is desired. An averaging method may be mainly used. Particularly, by averaging brain waves measured based on stimulus onset time, it is possible to remove brain waves, which are not related to a stimulus, and to pick out only a related potential, that is, a brain activity commonly associated with stimulus processing.

As ERP has a high time resolution, it is closely related to a research on cognitive function. ERP is an electrical phenomenon that is evoked by an external stimulus or is related to an internal state. According to types of stimuli, ERPs may be classified into auditory sense-related potentials, sight-related potentials, somatic sense-related potentials and olfactory sense-related potentials. According to properties of stimuli, ERPs may be classified into exogenous ERPs and endogenous ERPs. Exogenous ERPs have a waveform determined by an external stimulus, are related to automatic processing, and mainly appear in the initial phase of being given the stimulus. For example, exogenous ERPs are brainstem potentials. On the other hand, endogenous ERPs are determined by an internal cognitive process or a psychological process or state, irrespective of stimuli, and are related to 'controlled processing'. For example, endogenous ERPs are P300, N400, P600, CNV (Contingent Negative Variation), etc.

Names given to ERP peaks normally include a polarity and a latent period, and the peak of each signal has an individual definition and meaning. For example, the positive potential is P, the negative potential is N, and P300 means a positive peak measured about 300 ms after the onset of a stimulus. In addition, 1, 2, 3 or a, b, c and the like are applied according to the order of appearance. For example, P3 means a third positive potential in waveform after the onset of a stimulus.

Hereinafter, various ERPs will be described.

For example, N100 is related to a response to an unpredictable stimulus.

MMN (Mismatch Negativity) may be generated not only by a focused stimulus but also by non-focused stimulus. MMN may be used as an indicator for whether or not a sense memory (echoic memory) operates before initial attention. P300, which will be described below, appears in a process of paying attention and making judgment, while MMN is analyzed as a process occurring in the brain before paying attention.

For another example, N200 (or N2) is mainly generated according to visual and auditory stimuli and is related to short-term memory or long-term memory, which are types of memories after attention, along with P300 described below.

For yet another example, P300 (or P3) mainly reflects attention to a stimulus, stimulus cognition, memory search and alleviation of uncertain feeling and is related to perceptual decision distinguishing stimuli from outside. As the generation of P300 is related to a cognitive function, P300 is generated irrespective of types of presented stimuli. For example, P300 may be generated in auditory stimuli, visual stimuli and somatic stimuli. P300 is widely applied to a research on brain-computer interface.

For yet another example, N400 is related to language processing and is caused when a sentence or an auditory stimulus with a semantic error is presented. In addition, N400 is related to a memory process and may reflect a process of retrieving or searching information from long-term memory.

For yet another example, as an indicator showing reconstruction or recollective process, P600 is related to a process of processing a stimulus more accurately based on information stored in long-term memory.

For yet another example, CNV refers to potentials appearing for 200~300 ms and even for a few seconds in the later phase. It is also called slow potentials (SPs) and is related to expectancy, preparation, mental priming, association, attention and motor activity.

For yet another example, ERN (Error-Related Negativity) or Ne (error negativity) is an event-related potential (ERP) generated by a mistake or an error. It may occur when a subject makes a mistake in a sensorimotor task or a similar task. More particularly, when a subject cognizes a mistake or an error, ERN is generated and its negative peak appears mainly in the frontal and central zones for about 50~150 ms. Especially, it may appear in a situation, where a mistake related to motor response is likely to occur, and may also be used to indicate a negative self-judgment.

Hereinafter, the major features of ERN will be described in more detail.

FIG. 1 is a view illustrating a general waveform of ERN according to one form of the present disclosure.

Referring to FIG. 1, negative potential values are depicted above the horizontal axis, and positive potential values are depicted below the horizontal axis. In addition, it can be confirmed that an ERP with a negative peak value is generated within a predetermined time range after a response onset for an arbitrary motion. Herein, the response may mean a case where a mistake or an error is made (Error Response). In addition, the predetermined time range may be about 50~150 ms. Alternatively, the predetermined time range may be about 0~100 ms. Meanwhile, in the case of a correct response, an ERP is generated which has a relatively smaller negative peak than ERN.

As an ERP of initial negativity, ERN is time-locked until a response error occurs. In addition, ERN is known to reflect the reinforcement activity of a dopaminergic system related to behavioral monitoring. ERN includes the fronto-striatal loop including the rostral cingulate zone. Meanwhile, dopamine is associated with the reward system of brain that usually forms a specific behavior and motivates a person thereby providing pleasure and reinforced feelings. When a behavior obtaining an appropriate reward is repeated, it is learned as a habit. In addition, more dopamine is released through emotional learning, and a new behavior is attempted due to the release of dopamine. Thus, reward-driven learning is called reinforcement learning.

In addition, ERN may be generated in 0~100 ms after the onset of an erroneous response that is caused during an interference task (for example, Go-noGo task, Stroop task, Flanker task, and Simon task) through the frontal cortex lead.

In addition, together with CRN described below, ERN is known to reflect a general behavior monitoring system that can distinguish a right behavior and a wrong behavior.

In addition, the fact that ERN reaches a maximum amplitude at the frontal cortex electrode is known to reflect that an intracerebral generator is located in the rostral cingulate zone or the dorsal anterior cingulate cortex (dACC) zone.

In addition, ERN may show a change of amplitude according to a negative emotional state.

In addition, ERN may be reported even in a situation where behavioral monitoring is performed based on external evaluation feedback processing unlike internal motor expression, and may be classified as FRN described below.

In addition, ERN may be generated not only when having cognized a mistake or an error but also before cognizing the mistake or the error.

In addition, ERN may be generated not only as a response to his/her own mistake or error but also as a response to a mistake or error of others.

In addition, ERN may be generated not only as a response to a mistake or an error but also as a response to anxiety or stress for a predetermined performance task or object.

Meanwhile, for yet another example, being an event-related potential (ERP) that is generated after ERN, Pe (Error Positivity) is an ERP with a positive value, which is generated mainly at the frontal cortex electrode in about 150~300 ms after a mistake or an error. Pe is known as a reaction that realizes a mistake or an error and pays more attention. In other words, Pe is related to an indicator of a conscious error information processing process after error detection. ERN and Pe are known as ERPs related to error monitoring.

Hereinafter, the major features of Pe will be described in more detail.

Figure 2:
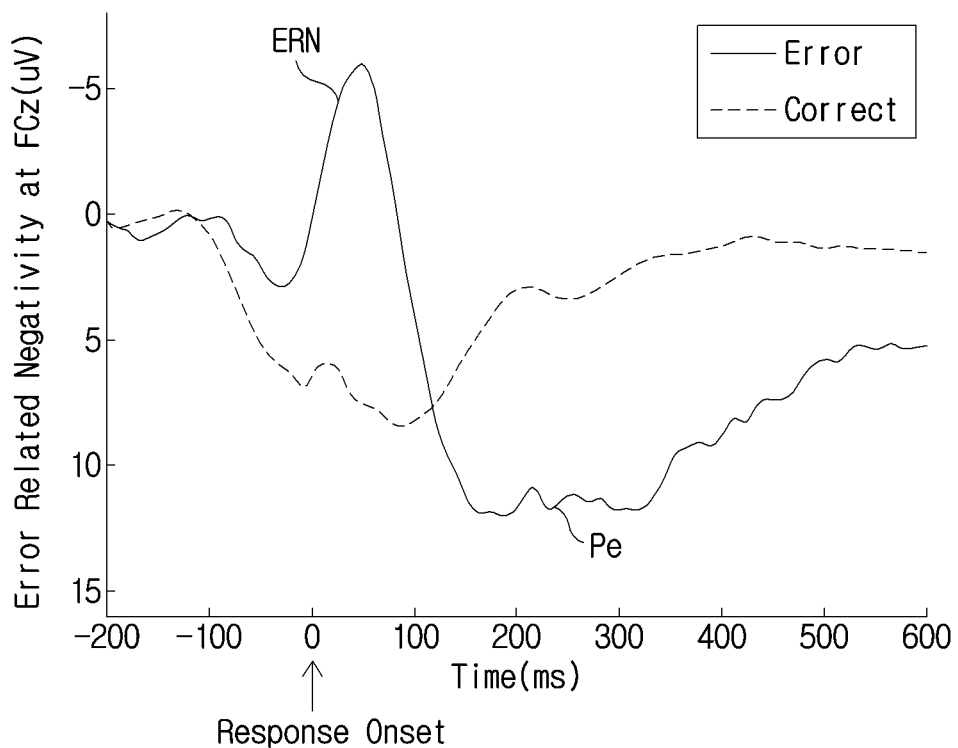
FIG. 2 is a view illustrating general waveforms of ERN and Pe according to one form of the present disclosure.

FIG. 2 is a view illustrating general waveforms of ERN and Pe according to another form of the present disclosure.

Referring to FIG. 2, negative potential values are depicted above positive potential values. In addition, it can be confirmed that an ERP with a negative peak value, that is, an ERN is generated within a first predetermined time range after a response onset for an arbitrary motion. Herein, the response may mean a case where a mistake or an error is made (Error Response). In addition, the first predetermined time range may be about 50~150 ms. Alternatively, the first predetermined time range may be about 0~200 ms.

In addition, it can be confirmed that an ERP with a positive peak value, that is, a Pe is generated within a second predetermined time range after the onset of the ERN. In addition, the second predetermined time range may be about 150~300 ms after an error onset. Alternatively, the second predetermined time range may mean about 200~400 ms.

Figure 3:
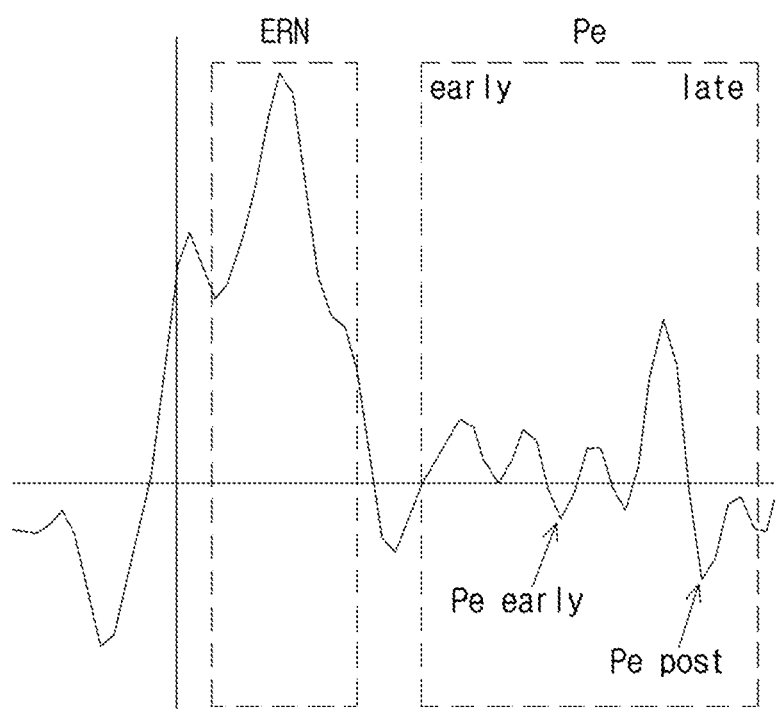
FIG. 3 is a view illustrating a deflection characteristic of Pe according to another form of the present disclosure.

FIG. 3 is a view illustrating a deflection characteristic of Pe in one form of the present disclosure.

Referring to FIG. 3, like P3, Pe has a wide deflection characteristic, and the plexus generator includes not only the areas of posterior cingulate cortex and insula cortex but also more anterior cingulate cortex.

In addition, Pe may reflect an emotional evaluation of an error and an attention to a stimulus like P300. In addition, ERN indicates a conflict between a right response and a wrong response, and Pe is known to be a response that realizes a mistake and pays more attention. In other words, ERN may be generated in a process of detecting a stimulus, and Pe may be generated depending on attention in a process of processing a stimulus. When ERN and/or Pe have relatively large values respectively, it is known that the values are related to an adaptive behavior intended to respond more slowly and more accurately after a mistake.

Figure 4A:
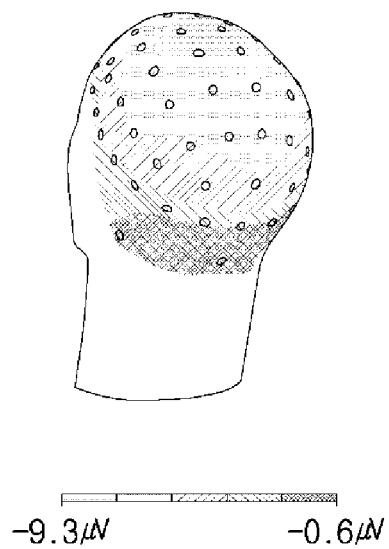
FIGS. 4A and 4B are views respectively illustrating measurement areas of ERP and Pe in one form of the present disclosure.
Figure 4B:
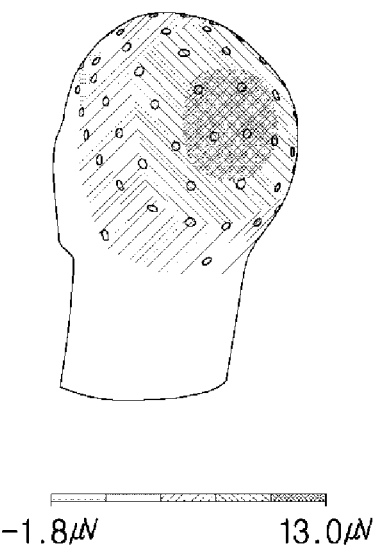

FIGS. 4A and 4B are views illustrating measurement areas of ERP and Pe according to one form of the present disclosure.

ERN and Pe are known as ERPs related to error monitoring. Regarding the measurement areas of ERN and Pe, a largest negative value and a largest positive value may normally be measured in the central area. However, there may be a little difference according to measurement conditions. For example, FIG. 4A is the main area where ERN is measured, and the largest negative value of ERN may normally be measured in the midline frontal or central zone (that is, FCZ). In addition, FIG. 4B is the main area where Pe is measured, and a large positive value of Pe may normally be measured in a posterior midline zone as compared to ERN.

Meanwhile, for yet another example, FRN (Feedback-Related Negativity) is an event-related potential (ERP) that is related to error detection obtained based on external evaluation feedback. ERN and/or Pe detect an error based on an internal monitoring process. However, in the case of FRN, when being obtained based on external evaluation feedback, it may operate similarly to the process of ERN.

In addition, FRN and ERN may share many electrophysiological properties. For example, FRN has a negative peak value at the frontal cortex electrode in about 250~300 ms after the onset of a negative feedback and may be generated in the dorsal anterior cingulate cortex (dACC) zone like ERN.

In addition, like ERN, FRN may reflect an activity of reinforcement learning by a dopaminergic system. In addition, FRN normally has a larger negative value than a positive feedback and may have a larger value for an unforeseen case than for a predictable result.

Figure 5:
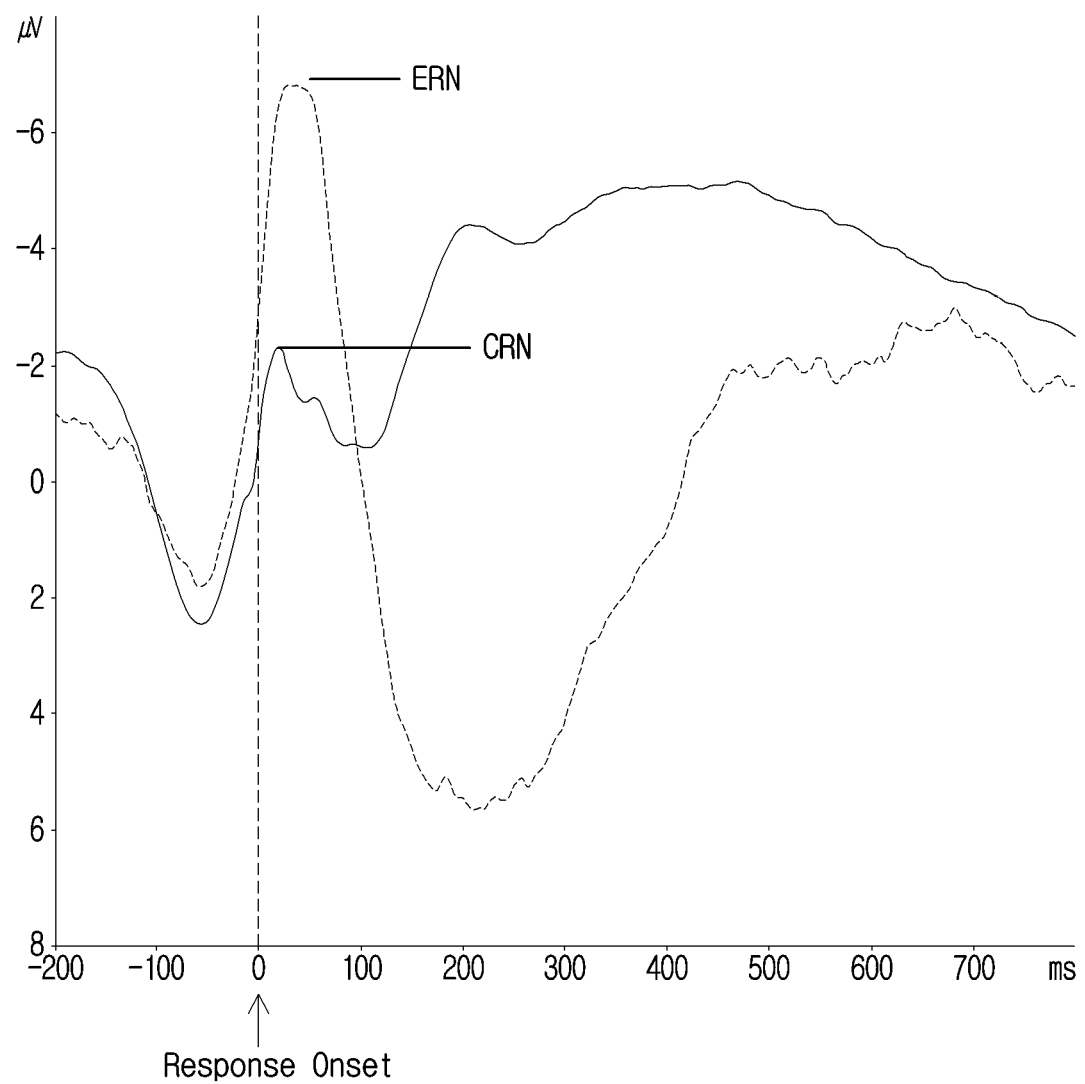
FIG. 5 is a view illustrating general waveforms of ERN and CRN according to one form of the present disclosure.

For yet another example, CRN (Correct-Related Negativity) is an ERP generated by a correct trial and is a negative value that is smaller than ERN. Like ERN, CRN may be generated in the initial latent period (for example, 0~100 ms). FIG. 5 is a view illustrating general waveforms of ERN and CRN in one form of the present disclosure.

For yet another example, Pc (Correct Positivity) is an event-related potential generated following CRN. It is an event-related potential generated in about 150~300 ms after the onset of correct response. The relation between CRN and Pc may be similar to the relation between ERN and Pe.

Meanwhile, ERPs may be classified into stimulus-locked ERPs and response-locked ERPs. The stimulus-locked ERPs and the response-locked ERPs may be divided according to criteria like evoking cause of ERP and response time. For example, an ERP evoked from a moment when a word or a picture is presented to a user from outside may be called a stimulus-locked ERP. In addition, for example, an ERP evoked from a moment when a user speaks or pushed a button may be called a response-locked ERP. Accordingly, based on the above-described criterion, in general, stimulus-locked ERPs are N100, N200, P2, P3, etc., and response-locked ERPs are ERN, Pe, CRN, Pc, FRN, etc.

Meanwhile, brain waves may be classified according to manifesting motives. Brain waves may be classified into spontaneous brain waves (spontaneous potentials) manifested by a user's will and evoked brain waves (evoked potentials) that are naturally manifested according to external stimuli irrespective of the user's will. Spontaneous brain waves may be manifested when a user moves on his/her own or imagines a movement, while evoked brain waves may be manifested by visual, auditory, olfactory and tactile stimuli, for example.

Meanwhile, brain wave signals may be measured in accordance with the International 10-20 system. The International 10-20 system determines measurement points of brain wave signals on the basis of the relationship between the location of an electrode and the cerebral cortex areas.

Figure 6:
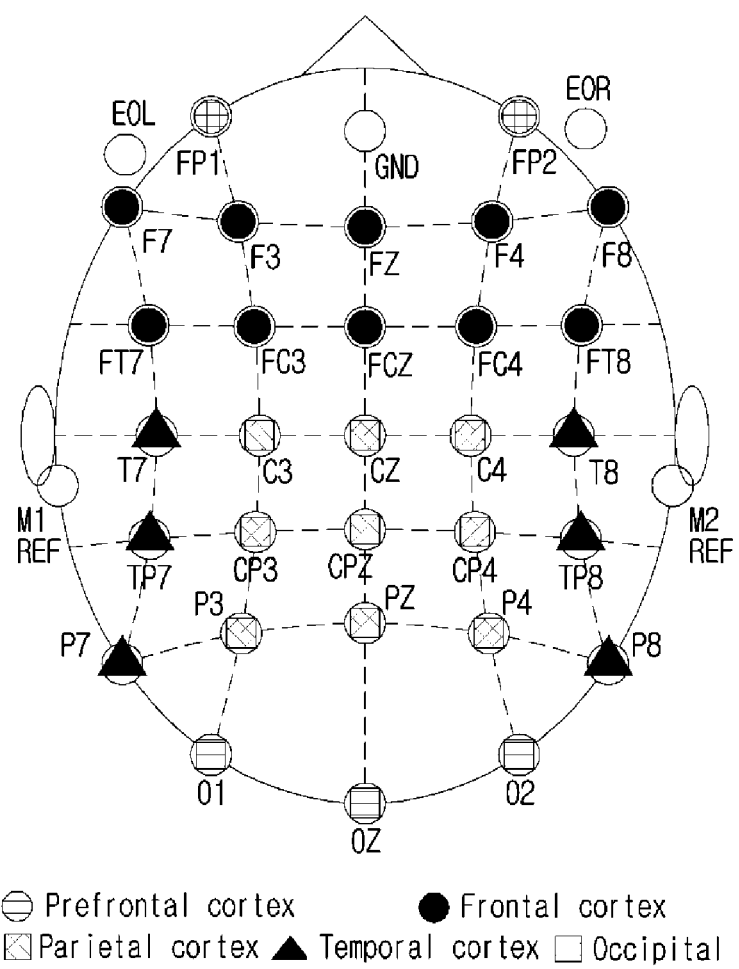
FIG. 6 is a view illustrating EEG measurement channels corresponding to cerebral cortex areas in one form of the present disclosure.

FIG. 6 is a view illustrating EEG measurement channels corresponding to the cerebral cortex areas according to one form of the present disclosure.

Referring to FIG. 6, brain areas (Prefrontal cortex FP1, FP2; Frontal cortex F3, F4, F7, F8, FZ, FC3, FC4, FT7, FT8, FCZ; Parietal cortex C3, C4, CZ, CP3, CP4, CPZ, P3, P4, PZ; Temporal cortex T7, T8, TP7, TP8, P7, P8; Occipital cortex O1, O2, OZ) correspond to 32 brain wave measurement channels. For each of the channels, data may be obtained and analysis may be performed for each cerebral cortex area by using the data.

Figure 7:
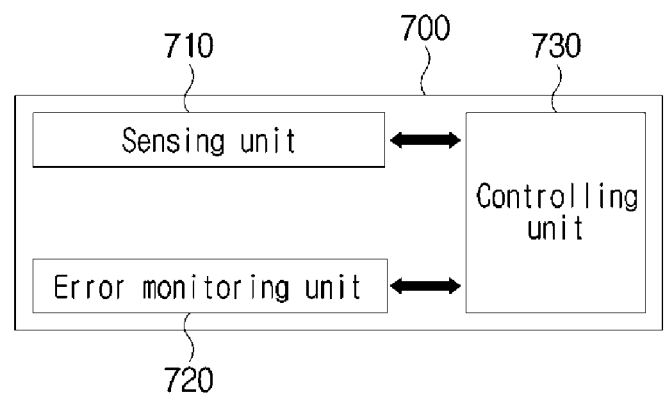
FIG. 7 is a block diagram illustrating a configuration of a mobility controlling apparatus using error monitoring according to another form of the present disclosure.

FIG. 7 is a block diagram illustrating a configuration of a mobility controlling apparatus using error monitoring according to another form of the present disclosure.

Referring to FIG. 7, a mobility controlling apparatus 700 may include a sensing unit 710, an error monitoring unit 720 and/or a controlling unit 730. It should be noted, however, that only some of the components necessary for explaining the present form are shown, and the components included in the mobility controlling apparatus 700 are not limited to the above-described example. For example, two or more constituent units may be implemented in one constituent unit, and an operation performed in one constituent unit may be divided and executed in two or more constituent units. Also, some of the constituent units may be omitted or additional constituent units may be added.

A mobility controlling apparatus of the present disclosure may perform monitoring for error generation by using response-locked ERPs. In addition, as the monitoring is performed, a mobility may be controlled. A sensing unit 710 in one form of the present disclosure may collect ERPs for at least one passenger in a mobility for a predetermined time. In addition, an error monitoring unit 720 may determine an error factor by analyzing the ERPs that are collected for the predetermined time. In addition, a controlling unit 730 may perform a mobility feedback based on the error factor that is determined in the error monitoring unit 720.

Meanwhile, the mobility may encompass the meanings of vehicle, moving/transport apparatus and the like.

Specifically, a mobility controlling apparatus of the present disclosure may collect an ERP for at least one passenger in a mobility for a predetermined time.

Herein, the ERP may mean a response-locked ERP. In addition, the response-locked ERP may include ERN, Pe, CRN, Pc and FRN. In addition, apart from the ERN, Pe, CRN, Pc and FRN, other ERPs obtained after a response occurs (that is, response onset) may be included. In addition, the response-locked ERP may include a plural of ERPs.

In addition, herein, collecting the ERP for a predetermined time may include a process of measuring a brain wave signal of at least one passenger in a mobility and detecting an ERP from the measured brain wave signal.

In FIGS. 1 to 6, as described above, ERN, Pe, CRN, Pc and/or FRN may be generated as responses to wrong behaviors like an error or a mistake, or responses to right behaviors. Accordingly, if the ERP is used, it is possible to judge whether or not a corresponding passenger has performed a wrong behavior. Also, based on the judgement, a mobility may be controlled to suit a purpose.

For example, when a driver has to make a right turn but makes a left turn, or when a driver has to make a left turn but continues to drive straight, ERN and/or Pe may be generated.

For another example, while driving according to a guide of a navigation system, if a driver fails to perform a movement according to the guide, ERN and/or Pe may be generated.

For yet another example, when a driver is in traffic, takes a course for the first time or undergoes a tense and stressful situation on road, ERN and/or Pe may be generated.

In addition, the predetermined time may be about 0~400 ms after the onset of a specific response. In addition, the predetermined time may include a time range where the above-described response-locked ERP can be obtained. In addition, the predetermined time may vary according to the type of a response-locked ERP and may have a plural of time ranges. For example, a first time range may be given to obtain a first ERP, and a second time range may be given to obtain a second ERP.

Figure 8:
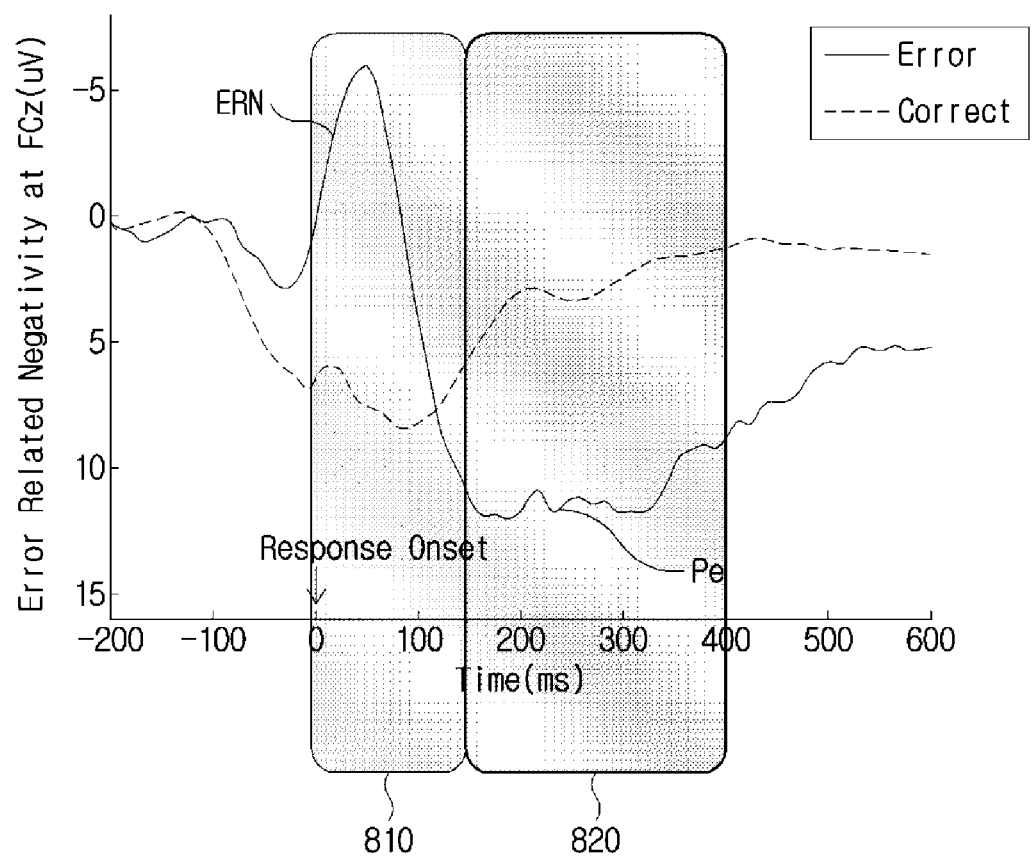
FIG. 8 is a view illustrating a measurement time range, when target ERPs are ERN and Pe, according to one form of the present disclosure.

For example, when a first ERP is ERN and a second ERP is Pe, a first time range may be about 0~150 ms that is the main measurement section of ERN, and a second time range may be about 150~400 ms that is the main measurement section of Pe. FIG. 8 is a view illustrating a measurement time range, when target ERPs are ERN and Pe. Referring to FIG. 8, ERN may be obtained in a first time range 810, and Pe may be obtained in a second time range 820.

For another example, when a first ERP is ERN and a second ERP is CRN, a first time range may be about 0~200 ms that is the main measurement section of ERN, and a second time range may be about 0~200 ms that is the main measurement section of CRN.

In addition, the passenger may include not only the driver in a mobility but also another passenger.

A mobility controlling apparatus of the present disclosure may determine an error factor by analyzing an ERP that is collected for a predetermined time.

Herein, the analysis may include a process of comparing the amplitude of the ERP, which is collected for the predetermined time, with a predetermined threshold.

Figure 9:
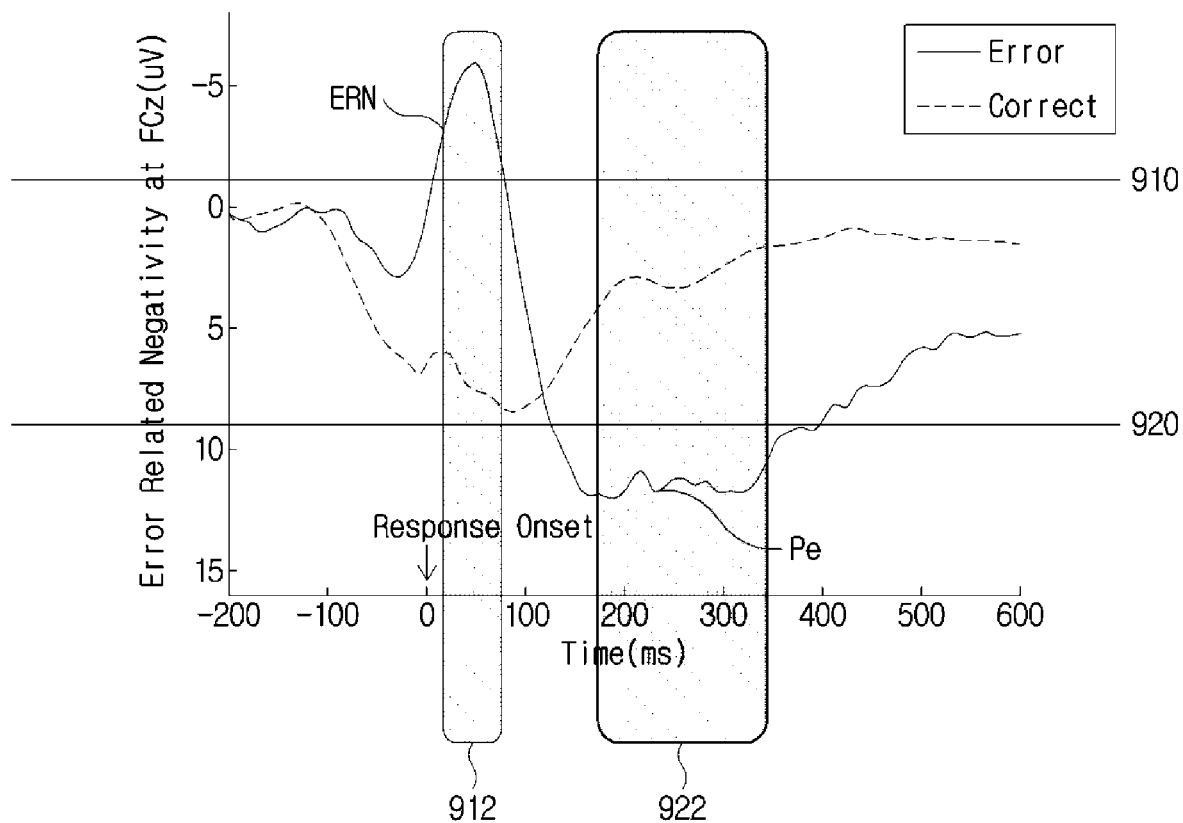
FIG. 9 is a view illustrating a process of comparing a target ERP with a predetermined threshold, when target ERPs are ERN and Pe respectively, according to another form of the present disclosure.

Meanwhile, the threshold may be a preset value or a value input by a user. In addition, the threshold may have a different amplitude for each passenger from whom an ERP is collected. For example, it may be a value reflecting the brain wave signal characteristic of each passenger. In order to reflect the analysis result of the brain wave signal characteristic, a predetermined learning process may be performed in advance for response-locked ERP characteristics displayed in a passenger's brain wave signal. In addition, the threshold may vary according to the type of ERP and may have a plural of thresholds. FIG. 9 is a view illustrating a process of comparing a target ERP and a predetermined threshold, when target ERPs are ERN and Pe respectively, according to another form of the present disclosure. Referring to FIG. 9, in the case of ERN, its amplitude may be compared with a first threshold 910. In the case of Pe, its amplitude may be compared with a second threshold 920.

In addition, the analysis may include a process of judging whether or not the amplitude of the ERP is equal to or greater than a predetermined threshold (that is, exceeds a predetermined threshold range) during a predetermined time interval. Referring to FIG. 9, in the case of ERN, the amplitude of ERN may be compared with a first threshold 910 to see whether or not the amplitude of ERN is equal to or greater than the first threshold 910 during a third time range 912. In the case of Pe, the amplitude of Pe may be compared with a second threshold 920 to see whether or not the amplitude of Pe is equal to or smaller than the second threshold 920 during a fourth time range 922.

In addition, the analysis may be performed by using a brain wave signal template of each passenger. Herein, a brain wave signal template may mean a brain wave signal in a time domain, which is obtained beforehand within a predetermined time range after a response onset for an arbitrary movement. The response may include an error, a mistake, a correct response and the like. The ready-made brain wave signal template may be scaled in the analysis process. In other words, the amplitude of a brain wave signal graph may be increased or decreased at a predetermined rate. For example, the analysis may be performed by comparing an amplitude-time graph waveform of a single ERP and/or a plural of ERPs obtained for a predetermined time with the brain wave signal template that is determined beforehand. Here, the arbitrary movement may be a predetermined one. For example, it may include events like the 10 gross negligence cases of traffic rules. The brain wave signal template may be obtained through a virtual simulation process or through a predetermined learning process.

Meanwhile, the analysis may be preceded by a process of cognizing the onset of an ERP by using a time when the characteristic of a brain wave signal appears and/or using the pattern of a brain wave signal. In addition, the analysis may include a processing of extracting an ERP.

In addition, an ERP used for the analysis may be a statistical value of ERP collected for a predetermined time. For example, the statistical value may mean an average value, a weighted average value, a maximum value and a minimum value.

As described above, an error factor may be determined by analyzing an ERP. In other words, by performing the analysis, it may be determined whether or not a predetermined ERP obtained from the passenger is meaningful information for mobility controlling.

For example, when the amplitude of an obtained ERP is above or below a predetermined threshold (that is, an obtained ERP is out of a predetermined threshold range), a mobility controlling apparatus may determine a predetermined event (or movement) related to the ERP as an error factor for a passenger.

The predetermined event related to the ERP may include a movement of a passenger himself, who causes the ERP, or of another person. In addition, it may include the movement of another mobility.

For example, when a driver has to make a right turn but makes a left turn or when a driver has to make a left turn but continues to drive straight, the corresponding event may be determined as an error factor for the driver.

For another example, while driving according to a guide of a navigation system, if a driver fails to perform a movement according to the guide, the corresponding event may be determined as an error factor of the driver.

For yet another example, while driving according to a guide of a navigation system, even if a driver fails to perform a movement according the guide, as long as the amplitude of a corresponding ERP is within a predetermined threshold range, the movement may not be determined as an error factor. In this case, it may be understood that the driver has intentionally chosen a different route from the guide of the navigation system.

Meanwhile, an ERP and a predetermined event related thereto may have a mapping relationship with each other. For example, depending on the amplitude (size) or waveform of an obtained ERP, a predetermined event may be mapped as shown in the example of Table 1.

TABLE 1

| Event-related potential (ERP) | Amplitude of event | Specific event |
| --- | --- | --- |
| ERP > First threshold | Large | First event |
| First threshold ≥ ERP & ERP ≥ Second threshold | Middle | Second event |
| ERP < Second threshold | Small | Third event |

Referring to Table 1, an event-related potential is ERP, and the amplitude of an event may mean the seriousness of an event taking place. A specific event may be classified into a first event, a second event and a third event according to each step, and the classification may vary according to passengers. In addition, a same event may be included in multiple steps.

For example, a first event has high seriousness and may include 10 gross negligence cases of traffic rules like driving over centerline and violation of traffic sign. The 10 gross negligence cases of traffic rules may be presented as in Table 2.

TABLE 2

| No | 10 Gross Negligence Events | Details |
| --- | --- | --- |
| 1 | Violation of traffic sign or instruction | ⓐ A case of violating a signal or instruction given by a police officer (including an exemplary driver and an MP (Military Police)) directing traffic. |
| | | ⓑ A case of not following but violating a traffic signal |
| | | ⓒ In the case of causing an accident by obstructing the way of other vehicles in a zone with PPLT (Protected/Permitted Left-Turn) sign, the responsibility for traffic sign violation cannot be avoided. |
| 2 | Driving over centerline | ⓐ Driving over centerline and crossing, making U-turn and driving backward on the highways (expressways). |
| | | ⓑ Even if only a part of a vehicle slightly steps on or crosses the centerline, it is equivalent to driving over centerline. |
| | | ⓒ In the case of crossing over the centerline in an irresistible or unavoidable situation like collision or icy road, it is not considered as driving over centerline. |
| | | ⓓ Private centerlines installed by residents in apartment complexes or residential areas are not centerlines. |
| 3 | Overspeed exceeding 20 km/h | ⓐ An accident taken place while driving at a speed exceeding the speed limit of 20 km/h |
| 4 | Violation of overtaking and method thereof | ⓐ An accident taken place while overtaking in case another vehicle is driven in the left lane alongside the vehicle ahead, |
| | | ⓑ in case the vehicle ahead is overtaking another vehicle, or overtaking in an intersection, a ramp or a tunnel. |
| | | ⓒ Overtaking prohibited areas: Intersection, bend, top of hill, downhill, bridge, tunnel, and other places with probation sign |
| | | ⓓ Prohibited cases of overtaking: vehicles ahead advancing side by side, following the vehicle ahead overtaking another vehicle, other cases prohibited by laws |
| 5 | Railroad crossing violation | ⓐ At railroad crossing, it is necessary to stop first and then safely cross. |
| 6 | Violation related to crosswalk | ⓐ Accident at a crosswalk with traffic lights- Applicable only when the stop signal for vehicles and the walk signal are on. |
| | | ⓑ Accident at a crosswalk without traffic light- Applicable only within the crosswalk mark |
| | | ⓒ If a victim of an accident was riding a bicycle or a motorcycle, he/she cannot be protected as a pedestrian. |
| 7 | Driving without license | ⓐ A case of driving a vehicle without license |
| | | ⓑ A case of driving a vehicle during the revocation or suspension period of license |
| | | ⓒ A case of driving a vehicle that the driver's license does not cover |
| | | ⓓ Along with criminal responsibility, even if a driver is insured, he/she cannot receive |

TABLE 2-continued

| No | 10 Gross Negligence Events | Details |
|---|---|---|
| | | insurance. |
| | | ⓔ In case the license is returned due to excessive penalty points but the administrative measure has not been taken, the accident is not categorized under driving without license. |
| 8 | Drunk driving | ⓐ In case the level of alcohol exceeds 0.5 ml in 1 ml of blood |
| | | ⓑ In case 0.25 ml or higher level of alcohol is detected in 1l of breath |
| | | ⓒ In case the breath alcohol level (BAL) is 0.05%, drunk driving is conducted. |
| 9 | Sidewalk trespassing | ⓐ A case of trespassing a sidewalk or driving in violation of a method of crossing a sidewalk |
| 10 | Starting with a door open | ⓐ A case of driving in violation of the passenger fall prevention duty → A case of pulling over or staring with a door open |

A mobility controlling apparatus of the present disclosure may perform mobility feedback based on the error factor.

Herein, the mobility feedback may mean controlling a predetermined apparatus included in a mobility. In addition, the mobility feedback may mean controlling a predetermined apparatus that is included in a mobility to reflect a passenger's intention in the mobility.

For example, when a driver has to make a right turn but makes a left turn or when a driver has to make a left turn but continues straight, a mobility controlling apparatus of the present disclosure may provide the driver with a guiding message as a mobility feedback saying that the vehicle has deviated from the original route due to the corresponding movement.

For another example, when an obtained ERP continues to be out of a predetermined threshold range on the road, a mobility controlling apparatus of the present disclosure may judge that a driver is under stress for the current route. In addition, a mobility controlling apparatus of the present disclosure may provide the driver with a new route.

For yet another example, a mobility controlling apparatus of the present disclosure may control an autonomous driving system by using error monitoring. Generally, since there is no quantitative rating scale or method for a driver's evaluation of an autonomous driving system except a survey for autonomous driving experience after the end of driving, there is no method of revising a decision-making model of an autonomous driving system in real time or immediately giving a feedback for a wrong decision. Accordingly, by performing error monitoring using a response-locked ERP, real-time evaluation and/or feedback for an autonomous driving system may be performed.

Specifically, based on the characteristic of an ERP of brain wave generated by a mistake or an error, it is possible to recognize that a decision made by an autonomous driving system has been judged to be a mistake or an error by a user. Accordingly, if a response-locked ERP is observed in a user's brain wave while an autonomous driving system is operated on the road, a decision-making model may be updated by giving a negative feedback to the corresponding decision-making of the autonomous driving system. While autonomous driving with a brain wave electrode attached on a user's FCZ, brain wave monitoring may be performed. In this case, a response-locked ERP may be measured by considering each decision making in an autonomous driving system as a single event. When a peak with a negative value is observed within a predetermined time after the occurrence of the event, the event may be cognized as a mistake or an error. Information on the event, which is cognized as a mistake or an error, may be provided to an autonomous driving system. The predetermined time may be 50~150 ms. Meanwhile, when an autonomous driving system receives a feedback that a specific decision made in a specific situation has been judged to be a mistake or an error, such information may be stored in a database and the system may be updated. In other words, an autonomous driving system may revise a decision-making model so that when a same situation as a case, which is judged to be a mistake or an error, occurs later, another decision can be made. For example, when a user cognizes a frequent lane change on a highway as a mistake or an error and ERN is observed accordingly, an autonomous driving system may receive a feedback for the event information and may revise a decision-making model to select the decision of land change on a highway with a lower probability. In other words, an autonomous driving system may be trained in a way of reducing a weight of the corresponding decision making in a decision-making model.

Figure 10:
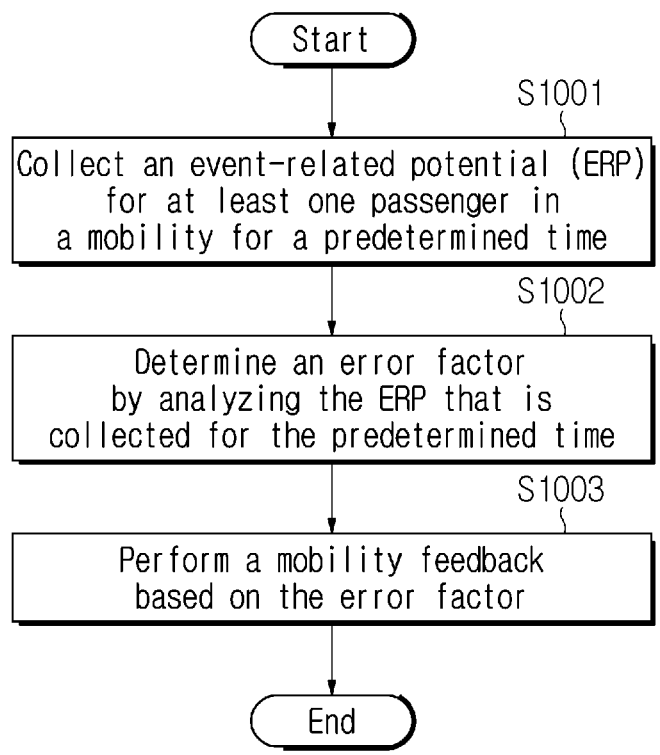
FIG. 10 is a flowchart illustrating a method of operating a mobility controlling apparatus using error monitoring in one form of the present disclosure.

FIG. 10 is a flowchart illustrating a method of operating a mobility controlling apparatus using error monitoring according to one form of the present disclosure.

Referring to FIG. 10, an ERP for at least one passenger in a mobility may be collected for a predetermined time (S1001).

Here, the ERP may include a response-locked ERP.

For example, the ERP may include at least one of ERN (Error-Related Negativity) and Pe (Error Positivity). In addition, the ERP may further include at least one of CRN (Correct-Related Negativity) and Pc (Correct Positivity).

Meanwhile, collecting the ERP for a predetermined time may include a process of measuring a brain wave signal of at least one passenger in a mobility and detecting an ERP from the measured brain wave signal.

Meanwhile, the collecting of an ERP for at least one passenger in the mobility for a predetermined time may include measuring a brain wave signal of the at least one passenger in the mobility and detecting the ERP from the measured brain wave signal.

In addition, an error factor may be determined by analyzing the ERP that is collected for the predetermined time (S1002). In addition, when the amplitude of the ERP collected for the predetermined time goes beyond the predetermined threshold range, the predetermined event may be determined as an error factor regarding the passenger.

Herein, the error factor may include at least one among the passenger causing the ERP, another person other than the passenger, and an operation of a mobility that is different from the mobility.

Herein, the analysis may mean comparing the amplitude of the ERP, which is collected for the predetermined time, and a predetermined threshold. In addition, the analysis may mean judging whether or not the amplitude of the ERP is within a predetermined threshold range during a predetermined time interval.

In addition, the analysis may be performed by using a brain wave signal template for the at least one passenger. In this case, the brain wave signal template may be a brain wave signal in a time domain, which is obtained beforehand within a predetermined time range after an error factor previously occurred.

In addition, the analysis may be preceded by a process of cognizing the onset of an ERP by using a time when the characteristic of a brain wave signal appears and/or using the pattern of a brain wave signal. In addition, the analysis may include a processing of extracting an ERP.

Meanwhile, the predetermined threshold may be differently determined according to at least one of the type of the ERP and the passenger from whom the ERP is obtained.

the predetermined event is derived from a mapping relationship between a plural of events and a comparison result between the amplitude of the ERP and the predetermined threshold.

Meanwhile, the predetermined threshold may include a first threshold and a second threshold, the predetermined event may include a first event, a second event and a third event. When the amplitude of the collected ERP exceeds the first threshold, the predetermined event may be mapped with the first event. When the amplitude of the collected ERP is smaller than the second threshold, the predetermined event may be mapped with the third event. When the predetermined event is neither the first event nor the third event, it may be mapped with the second event.

In addition, based on the error factor, mobility feedback may be performed (S1003).

Meanwhile, the mobility feedback may mean controlling a predetermined apparatus included in the mobility.

Although exemplary methods of the present disclosure are described as a series of operation steps for clarity of a description, the present disclosure is not limited to the sequence or order of the operation steps described above. The operation steps may be simultaneously performed, or may be performed sequentially but in different order. In order to implement the method of the present disclosure, additional operation steps may be added and/or existing operation steps may be eliminated or substituted.

Various forms of the present disclosure are not presented to describe all of available combinations but are presented to describe only representative combinations. Steps or elements in various forms may be separately used or may be used in combination.

In addition, various forms of the present disclosure may be embodied in the form of hardware, firmware, software, or a combination thereof. When the present disclosure is embodied in a hardware component, it may be, for example, an application specific integrated circuit (ASIC), a digital signal processor (DSP), a digital signal processing device (DSPD), a programmable logic device (PLD), a field programmable gate array (FPGA), a general processor, a controller, a microcontroller, a microprocessor, etc.

The scope of the present disclosure includes software or machine-executable instructions (for example, operating systems (OS), applications, firmware, programs) that enable methods of various forms to be executed in an apparatus or on a computer, and a non-transitory computer-readable medium storing such software or machine-executable instructions so that the software or instructions can be executed in an apparatus or on a computer.

What is claimed is:

1. A mobility controlling apparatus, the apparatus comprising:
a sensing unit configured to collect an Event-Related Potential (ERP) from a passenger in a mobility for a predetermined time;
an error monitoring unit configured to analyze the collected ERP and determine an error factor based on the analyzed ERP of the passenger, wherein the error factor corresponds to an event to which the passenger is not intended; and
a controlling unit configured to perform a mobility feedback based on the error factor,
wherein the error monitoring unit is configured to compare an amplitude of the collected ERP of the passenger with a predetermined threshold, and
wherein the predetermined threshold is differently determined based on at least one of a type of the collected ERP or the passenger from whom the ERP is obtained.

2. The apparatus of claim 1, wherein the ERP comprises at least one of Error-Related Negativity (ERN), Error Positivity (Pe), Correct-Related Negativity (CRN) or Correct Positivity (Pc).

3. The apparatus of claim 1, wherein the error monitoring unit is configured to determine the error factor based on ERPs collected from at least one of the passenger causing the ERP, or another passenger in the mobility, or an operation of another mobility.

4. The apparatus of claim 1, wherein the mobility feedback is used to control a predetermined apparatus included in the mobility.

5. The apparatus of claim 1, wherein, when the amplitude of the collected ERP is greater than the predetermined threshold, the error monitoring unit is configured to determine a predetermined event as the error factor regarding the passenger.

6. The apparatus of claim 5, wherein the predetermined event is derived from a mapping relationship between a plural of events and a comparison result between the amplitude of the collected ERP and the predetermined threshold.

7. The apparatus of claim 6, wherein:
the predetermined threshold includes a first threshold and a second threshold, and the predetermined event includes a first event, a second event, and a third event,
when the amplitude of the collected ERP exceeds the first threshold, the predetermined event is mapped with the first event,
when the amplitude of the collected ERP is smaller than the second threshold, the predetermined event is mapped with the third event, and
when the predetermined event is neither the first event nor the third event, the predetermined event is mapped with the second event.

8. The apparatus of claim 1, wherein:
the error monitoring unit is configured to analyze the collected ERP by using a brain wave signal template for the passenger, and
the brain wave signal template is a brain wave signal in a time domain, which is previously obtained within a predetermined time range after an error factor previously occurred.

9. A mobility controlling method, the method comprising:
collecting, by a sensing unit, an Event-Related Potential (ERP) from a passenger in a mobility for a predetermined time;
determining, by an error monitoring unit, an error factor by analyzing the collected ERP for the predetermined time, wherein the error factor corresponds to an event to which the passenger is not intended; and
performing, by a control unit, a mobility feedback based on the error factor,
wherein determining the error factor includes comparing an amplitude of the collected ERP of the passenger with a predetermined threshold, and
wherein the predetermined threshold is differently determined based on at least one of a type of the collected ERP or the passenger from whom the ERP is obtained.

10. The method of claim 9, wherein the ERP comprises at least one of Error-Related Negativity (ERN), Error Positivity (Pe), Correct-Related Negativity (CRN), or Correct Positivity (Pc).

11. The method of claim 9, wherein the error factor is determined based on ERPs collected from at least one of the passenger causing the ERP, or another passenger in the mobility, or an operation of another mobility.

12. The method of claim 9, further comprising:
controlling a predetermined apparatus included in the mobility with the mobility feedback.

13. The method of claim 9, wherein determining of the error factor comprises:
determining a predetermined event as the error factor regarding the passenger, when the amplitude of the collected ERP is greater than the predetermined threshold.

14. The method of claim 13, wherein the predetermined event is derived from a mapping relationship between a plurality of events and a comparison result between the amplitude of the collected ERP and the predetermined threshold.

15. The method of claim 14, wherein:
the predetermined threshold includes a first threshold and a second threshold, and the predetermined event includes a first event, a second event and a third event,
when the amplitude of the collected ERP exceeds the first threshold, the predetermined event is mapped with the first event,
when the amplitude of the collected ERP is smaller than the second threshold, the predetermined event is mapped with the third event, and
when the predetermined event is neither the first event nor the third event, the predetermined event is mapped with the second event.

16. The method of claim 9, wherein:
analyzing the collected ERP is performed with a brain wave signal template for the passenger, and
the brain wave signal template is a brain wave signal in a time domain, which is previously obtained within a predetermined time range after an error factor previously occurred.

17. A mobility controlling apparatus, the apparatus comprising:
a sensing unit configured to collect an Event-Related Potential (ERP) from a passenger in a mobility for a predetermined time;
an error monitoring unit configured to analyze the collected ERP and determine an error factor based on the analyzed ERP of the passenger, wherein the error factor corresponds to an event to which the passenger is not intended; and
a controlling unit configured to perform a mobility feedback based on the error factor, wherein:
the error monitoring unit is configured to analyze the collected ERP by using a brain wave signal template for the passenger, and
the brain wave signal template is a brain wave signal in a time domain, which is previously obtained within a predetermined time range after an error factor previously occurred.

18. The apparatus of claim 17, wherein the ERP comprises at least one of Error-Related Negativity (ERN), Error Positivity (Pe), Correct-Related Negativity (CRN) or Correct Positivity (Pc).

19. The apparatus of claim 17, wherein the error monitoring unit is configured to determine the error factor based on ERPs collected from at least one of the passenger causing the ERP, or another passenger in the mobility, or an operation of another mobility.

20. The apparatus of claim 17, wherein the mobility feedback is used to control a predetermined apparatus included in the mobility.

* * * * *